US009801525B2

(12) United States Patent
Eisenkolb et al.

(10) Patent No.: US 9,801,525 B2
(45) Date of Patent: Oct. 31, 2017

(54) METHOD FOR ASSEMBLING A COVER GLASS IN AN ENDOSCOPE AND ENDOSCOPE

(75) Inventors: Peter Eisenkolb, Tuttlingen (DE); Stefan Heseler, Tuttlingen (DE); Martin Lehmann, Zoznegg (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 248 days.

(21) Appl. No.: 13/291,801

(22) Filed: Nov. 8, 2011

(65) Prior Publication Data

US 2012/0123210 A1     May 17, 2012

(30) Foreign Application Priority Data

Nov. 8, 2010    (DE) .................. 10 2010 050 513

(51) Int. Cl.
*A61B 1/00*     (2006.01)
*A61B 1/04*     (2006.01)

(52) U.S. Cl.
CPC ........ *A61B 1/0011* (2013.01); *A61B 1/00096* (2013.01)

(58) Field of Classification Search
CPC .............. A61B 1/0011; A61B 1/00195; A61B 1/00096; A61B 1/00142; A61B 1/0055; B23K 1/19
USPC ................................. 600/112, 131, 160–177
See application file for complete search history.

(56) References Cited

U.S. PATENT DOCUMENTS

| | | | |
|---|---|---|---|
| 5,536,244 A | | 7/1996 | Muller et al. |
| 6,487,440 B2 * | | 11/2002 | Deckert et al. ............... 600/476 |
| 6,955,644 B2 * | | 10/2005 | Forkey et al. ................ 600/133 |
| 2006/0069308 A1 * | | 3/2006 | Renner et al. ................ 600/133 |
| 2008/0045991 A1 * | | 2/2008 | Mihalca ....................... 606/176 |

FOREIGN PATENT DOCUMENTS

| | | |
|---|---|---|
| DE | 3740417 A1 | 6/1989 |
| DE | 9309545 U1 | 8/1993 |
| DE | 10344109 A1 | 4/2005 |
| EP | 1370175 B1 | 10/2006 |
| WO | 9804948 A1 | 2/1998 |

OTHER PUBLICATIONS

German Search Report; Application No. DE 10 2010 050 513.7; dated Sep. 26, 2011; 4 pages.

* cited by examiner

*Primary Examiner* — Timothy J Neal
(74) *Attorney, Agent, or Firm* — Whitmyer IP Group LLC

(57) ABSTRACT

A method for assembling a cover glass in an endoscope and an endoscope with a cover glass. To assemble a cover glass in an endoscope, an uncoated cover glass is soldered into an intermediate ring, the cover glass soldered into the intermediate ring is provided with a coating, and the intermediate ring provided with the coated cover glass is joined into a sheath of the optical system of the endoscope.

17 Claims, 1 Drawing Sheet

METHOD FOR ASSEMBLING A COVER GLASS IN AN ENDOSCOPE AND ENDOSCOPE

CROSS-REFERENCE TO RELATED APPLICATIONS

The present application claims priority of German patent application No. 10 2010 050 513.7 filed on Nov. 8, 2010.

FIELD OF THE INVENTION

The present invention relates to a method for assembling a cover glass in an endoscope as well as an endoscope with such a cover glass.

BACKGROUND OF THE INVENTION

An endoscope typically includes an elongated shaft, which is suitable for insertion into a cavity, as well as a head, which can comprise junctions and operating elements as well as an eyepiece. In addition to, or in place of, the eyepiece, a junction for a video camera can be provided; frequently the eyepiece itself is configured for the connection of a video camera, which can be fastened for example to an eyecup. An optical system can be positioned within the shaft and head for retransmitting an endoscopic image from the distal end (that is, distant from the observer) of the endoscope to the proximal end (that is, close to the observer). For said purpose, an optical system can include in particular a distally mounted objective lens for recording the endoscope image, an image-relaying element and an ocular with eyepiece for visual observation of the retransmitted endoscopic image. The endoscope can be configured, in particular, with a rigid shaft and can comprise a rod lens arrangement as image retransmitter, but can also be configured semi-flexibly or flexibly with a glass fiber bundle as image retransmitter. The endoscope can comprise an illumination device for illuminating a cavity that is to be observed, and in some cases channels for endoscopic working instruments.

For hygienic reasons, endoscopes intended for medical purposes must be sterilizable. Sterilization today is primarily done by autoclaving, that is, by hot vapor at increased pressure, for example at 2 bar, and at a temperature of approximately 140 degrees C. However, optical systems of endoscopes are as a rule sensitive to hot vapor, which can penetrate during hot vapor sterilization and can result, for example, in glass corrosion. In addition, moisture that has penetrated into an optical system can result in coating of optical elements and thereby can impede functioning. For this reason, protective measures against penetration of hot vapor can be required, in particular the pressure conditions prevailing in the use of hot vapor sterilization. Such protective measures are also advantageous with other sterilization methods such as chemical sterilization as well as, for example, with technical applications in cavities that contain aggressive gaseous or liquid media.

In particular, the optical system can be enclosed in a vapor-proof tube that is of continuous construction or consists of a number of tubes or sheaths that are connected with one another and are vapor-proof. The proximal and distal ends of the tube in this case are each closed with cover glasses, which are connected in vapor-proof manner with the tube or with a sheath connected with the tube.

To produce a vapor-proof connection between a cover glass and the tube or with a sheath, it is a known practice to cement the cover glass with the tube or sheath, for example by spraying the cover glass with a synthetic substance, such as polyphenylsulfone (PPSU), which can also be used for example to construct the eyecup. PPSU, however, is not sufficiently resistant to chemicals used in disinfection and sterilization and can be discolored during the preparation. Other synthetics or cementing substances also have disadvantages concerning resistivity to sterilization and cannot always ensure a reproducible insulated connection, and/or may not sufficiently prevent or obstruct diffusion processes of moisture by the synthetic or cementing.

It is a known procedure from DE 37 40 417 A1, in case of a rigid endoscope lens system with a metallic tube that encloses the lenses and is closed on the distal end with a window, to coat the surrounding surface of the distal end window with a metallic film and to solder this metallic film with the tube inner surface.

According to WO 98/04948, an end window of an endoscope is cemented into an outer tube, inside which the optical system is enclosed, or into an intermediate part inserted into the outer tube, while the end window is additionally connected with the outer tube or the intermediate part by means of a soldered layer. For this purpose, a solderable ring-shaped layer is applied on at least one end surface of the end window.

Applying such a solderable metallic coating, however, constitutes additional expense. A desirable solution, therefore, would be not to perform the soldering with a prior applied metallic film but rather directly with the glass, which as a rule is a sapphire glass in this case. A cost-effective method for soldering sapphire glass is active soldering, in which a special solder, which in particular can contain silver, copper and titanium, is applied in a vacuum at a temperature of about 900 degrees C. or more. In this case, previous coating with a solderable layer is required. Under these conditions, however, an anti-reflecting coating, which is advantageous for improving the image quality at least on the inside of the cover glass, is destroyed. Such an anti-reflecting coating itself is not solderable. It is disclosed in U.S. Pat. No. 5,536,244 that an end window is soldered directly into a metallic frame that is inserted into the endoscope shaft and welded to it; no coating is mentioned.

SUMMARY OF THE INVENTION

It is the object of the present invention to provide a method for assembling a cover glass in an endoscope as well as an endoscope with such a cover glass, such that the aforementioned disadvantages are avoided. In particular, it is the object of the present invention to provide a simplified method with which an endoscope with a soldered cover glass is contained that comprises a coating, in particular an anti-reflecting coating, as well as a corresponding endoscope. As an alternative, the coating could, for instance, also be an anti-fog coating.

This object is achieved by means of a method as well as by an endoscope with the characteristics of the independent claims.

In an inventive method for assembling a cover glass in an endoscope, an uncoated cover glass is first soldered into an intermediate ring. The cover glass in this condition comprises no metallic coating, in particular. In the next step, the cover glass soldered into the intermediate ring is provided with a coating, in particular with a coating that serves to improve the optical properties of the cover glass and/or of the optical system of the endoscope. In the process, part of the coating can be precipitated on the intermediate ring, but without compromising its use. In an additional step, the intermediate ring, which supports the cover glass provided with the coating, is finally attached in a sheath of the endoscope. The sheath can be configured as a tube or part of the tube that at least partly surrounds the optical system of the endoscope or can be connected with the tube. In particular, the beam path of the endoscope runs through the sheath, and the cover glass can be configured as a distal end window, that is, as inlet window, or as proximal end window, that is, as outlet window, of the beam path or of the endoscopic image. The cover glass, in particular, is made of sapphire glass.

Because the cover glass is soldered into the intermediate ring that is attached in the sheath of the optical system of the endoscope, it is possible to make a gas-proof and fluid-proof connection, in particular one that is hermetically insulated, between the cover glass and the sheath and thereby a vapor-proof or hermetically insulated enclosure of the optical system. In addition, because the cover glass at first is inserted into the intermediate ring in uncoated condition and the coating is applied following this step, it is possible to avoid damage to the coating by the soldering process, for example by the mechanical handling, the thermal and/or chemical conditions in soldering. Finally, because the coating is applied onto the cover glass soldered into the intermediate ring, the coating process is facilitated and the quality of the coating improved. As a result, in particular it is possible to avoid the problem, which arises on coating a cover glass inserted into the sheath, that a coating can fail to be applied, or can be applied in insufficient quality, inside the sheath onto the inside of the cover glass. This can occur because the sheath typically protrudes by a multiple of the diameter of the cover glass beyond its inner surface. On the other hand, the intermediate ring does not extend out beyond the inner surface in the axial direction, or does so only by a fraction of the diameter of the cover glass. The surface of the cover glass that is to be coated is therefore not overshadowed to a considerable extent by the intermediate ring during the coating process and the coating process is not substantially disturbed. Coating can occur, for example, by vaporization.

In preferred manner, the cover glass is soldered into the intermediate ring by hard soldering, in particular by active brazing. As a result, a secure, temperature and chemical resistant, vapor-proof connection can be established between the cover glass and the intermediate ring. In addition, as a result lesser tensions are exerted on the cover glass than with other soldering methods. According to the invention, the use of hard soldering or active brazing is not restricted to a coating that is already present on the cover glass. In particular, a secure connection can be achieved by active brazing, without the necessity that a solderable layer has been previously applied on the cover glass. Sapphire glass is especially suited for this.

According to a preferred embodiment of the invention, the cover glass is soldered into the intermediate ring by first inserting the cover glass into the intermediate ring, so that a gap remains between a particularly cylindrical surrounding surface of the cover glass and a particularly likewise cylindrical inner surface of the intermediate ring. In the subsequent soldering process, the solder penetrates into the gap and at least partly fills it. As a result, an especially secure and firm connection can be established in especially simple manner between the cover glass and the intermediate ring. As well, a vapor-insulated connection can be established with the greatest possible security especially when the height of the gap is sufficient great that any remaining pores can be surrounded by solder and thus cause no lack of insulation.

It is advantageous, in addition, that the solder should form a fillet weld between a surrounding surface of the cover glass and a ring-shaped plane surface of the intermediate ring. As a result, additional security is ensured for achieving a firm, vapor-insulated connection.

According to a preferred embodiment of the invention, the coating is applied at least on the inside of the cover glass. A coating can also be applied on the outside of the cover glass, though damage can be caused to it from the cleaning and sterilization actions that are repeatedly required in using the endoscope, and thus this technique proves less useful as a rule than an inside coating. This has no disadvantageous consequences provided that part of the coating is deposited on the intermediate ring in addition to the surface of the cover glass.

According to an especially preferred embodiment of the invention, the coating is an anti-reflecting coating. Such an anti-reflecting coating improves the transmission and reduces undesired reflections inside the endoscope. According to the invention, the application and type of anti-reflecting coating is not restricted by the conditions of the soldering process.

Alternatively, the coating could also be an anti-fog coating.

Before joining the intermediate ring into the sheath, a drying agent can advantageously be applied in the sheath. Reference is made in this connection to patents DE 10344109 B4 and EP 1370175 B1, whose content is hereby incorporated into this application. By applying a drying agent, for example as taught by one of the referenced patents, it is possible to achieve the greatest possible security against coating the elements of the optical system when residual humidity is present or the slightest faults in insulation exist. Additional structural elements can likewise be inserted into the sheath as needed.

In addition it is preferable that the intermediate ring should be joined into the sheath of the endoscope by welding. This results in a durably firm and vapor-insulated connection. The additional advantage of welding is that any tensions exerted by the intermediate ring onto the cover glass are further reduced. It is also possible, however, to apply other joining techniques for connecting the intermediate ring with the sheath, for example welding or cementing.

According to a preferred embodiment of the inventive method, the sheath is an eyecup sheath that supports an eyecup and surrounds the proximal part of the optical system of the endoscope. In this case the cover glass serves as a proximal end window of the endoscope.

In preferred manner, the eyecup can be screwed onto the eyecup sheath. Because a prefabricated eyecup is screwed onto the sheath, errors from axial deviations as well as lurching errors can be to a great extent avoided; such errors can make themselves particularly felt when an electronic image recorder, for example a video camera, is attached to the eyecup, because for this the most precise possible axial arrangement is desirable.

An inventive endoscope comprises an elongated tube, which in particular can be of rigid or semi-flexible configuration, in whose interior at least one part of an optical system is positioned for retransmitting an endoscopic image from a distal to a proximal end of the endoscope. The optical system is closed off by a cover glass on the distal and/or proximal end, such that the cover glass is soldered without any intermediate coating into an intermediate ring that is joined into the sheath of the endoscope that is connected with the tube or forms the tube, and such that the cover glass is equipped with an anti-reflecting coating. The connections between the cover glass and the intermediate ring as well as between the intermediate ring and the sheath and/or tube are, in particular, insulated against vapor. The optical system of the endoscope is consequently preferably insulated against vapor or hermetically sealed.

It is understood that the aforementioned characteristics and those yet to be described can be applied not just in the particular indicated combination but also in other combinations or alone, without departing from the context of the present invention.

Further aspects of the invention can be seen from the subsequent description of a preferred embodiment and the appended drawings, which are as follows.

DETAILED DESCRIPTION OF THE INVENTION

Figure 1:
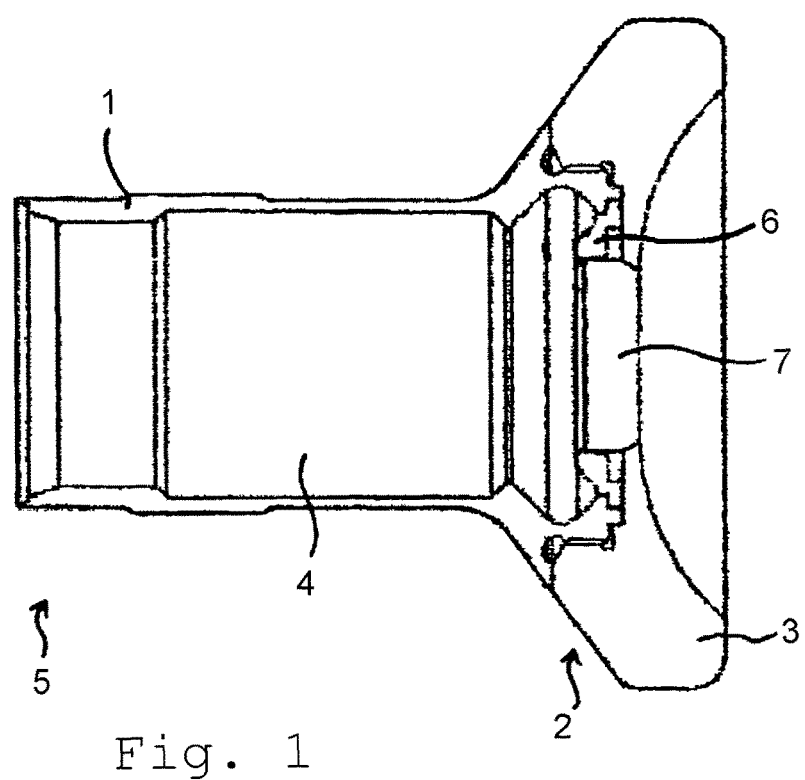
FIG. 1 shows a longitudinal section through the proximal end portion of an endoscope according to an embodiment of the invention.

According to FIG. 1, the proximal end portion of an endoscope includes an eyecup sheath 1, on whose proximal end 2 an eyecup 3 is screwed. The eyecup can be made of synthetic material, for example polyether ether ketone (PEEK), and in addition can be connected by cementing with the eyecup sheath 1. The eyecup sheath comprises an interior 4, which contains a proximal end portion of the optical system of the endoscope, which can include lenses or other optical elements, which can be enclosed in an interior tube (not illustrated). The eyecup sheath 1 converts at its distal end 5 into an outer tube that encloses the optical system or is connected with it (not illustrated); the outer tube can form the endoscope shaft. In particular, the eyecup sheath 1 is connected in vapor-proof manner with the outer tube. A possibly present inner tube, in addition, can be of vapor-proof configuration. The eyecup sheath 1 is usually a few centimeters in length, for example about 3 cm, with a typical diameter of the cover glass.

In the area of the proximal end 2 of the eyecup sheath 1, an intermediate ring 6 is inserted into the sheath and configured as a steel ring. The intermediate ring 6 supports a cover glass 7, which serves here as a proximal end window of the endoscope, and allows visual observation of the endoscopic image retransmitted by the optical system. A video camera can be mounted on the eyecup 3, such that the lens system of the video camera focuses the beams emanating from the cover glass onto an electronic image recorder (not illustrated). The cover glass is of plexiglass in the embodiment, but could also comprise curved surfaces that have an optical effect.

Figure 2:
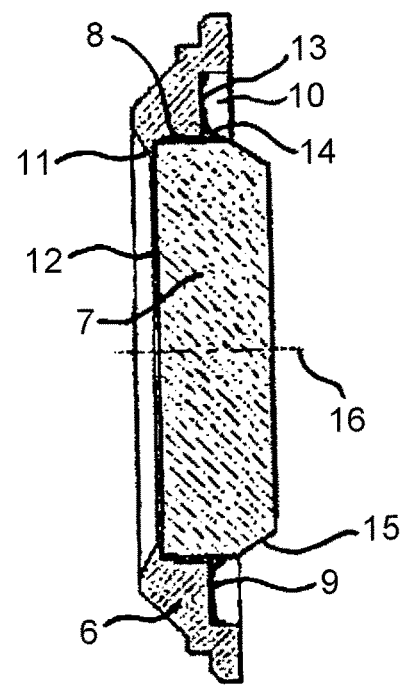
FIG. 2 shows an enlarged detail view of the proximal end of the endoscope of FIG. 1, likewise in longitudinal section.

As can be seen from the enlarged detail depiction in FIG. 2, a surrounding gap 8 is configured between a cylindrical inner wall of the intermediate ring 6 and a likewise cylindrical surrounding surface of the cover glass 7. To connect the cover glass 7 with the intermediate ring 6, through active brazing the solder 9 is applied into the surrounding groove 10 that develops through the positioning of the cover glass 7 in the intermediate ring 6. The liquid solder 9, through capillary forces, penetrates into the gap 8 and fills it to a considerable extent, such that even any possible gap between a ring-shaped protrusion 11 of the intermediate ring 6 pointing radially inward and the surface 12 of the cover glass that is internal with respect to the endoscope can be filled by the solder. The ring-shaped plain surface 13 of the intermediate ring 6 that forms the base of the groove can likewise be moistened with solder.

By filling the gap 8 with solder 9, the greatest possible security against leaks can be achieved, because any possibly remaining pores are sealed with solder and thus no leaks can be caused. For this purpose the gap 8 should have a sufficient height, which can be for example approximately 1 mm. The cylindrical surrounding surface of the cover glass 7 protrudes out in the axial direction beyond the cylindrical inner wall of the intermediate ring 6. Between the surrounding surface of the cover glass 7 and the ring-shaped plain surface 13, the remaining solder forms a fillet weld 14, which in addition contributes to insulation and security of the connection. The cover glass 7 comprises a surrounding bevel 15 outside the cylindrical surrounding surface. The optical axis of the cover glass 7 and/or of the optical system of the endoscope is identified with reference number 16 in FIG. 2.

To assemble the cover glass 7 in an endoscope, the cover glass 7 is first placed in the intermediate ring 6 adjacent with the radial protrusion 11. Then the cover glass 7, as explained in the foregoing, is connected in vapor-proof manner with the intermediate ring 6. An anti-reflecting coating is then applied on the free portion of the internal surface 11; this process is not essentially restricted by the intermediate ring 6. Any application of coating on portions of the intermediate ring 6 does not restrict its functioning. After applying drying agents in the eyecup sheath 1, the unit consisting of intermediate ring 6 and cover glass 7 is inserted into the eyecup sheath 1, by placing the intermediate ring 6 in the proximal end portion of the eyecup sheath 1 and by a joining process joining it in vapor-proof manner, in particular by soldering it. Finally, the eyecup 3 is screwed onto the eyepiece sheath 1. The eyecup 3 here protrudes beyond the cover glass on the bevel 15 so that the cover glass is secured in addition from falling out.

What is claimed is:

1. A method for assembling a cover glass in an endoscope, comprising the steps of:
    placing an uncoated cover glass into a groove in an intermediate ring adjacent a radial protrusion,
    soldering the uncoated cover glass to the intermediate ring,
    after the step of soldering, applying a coating to an internal surface of the uncoated cover glass connected to the intermediate ring to form a coated cover glass,
    applying a drying agent to an eyecup sheath of an optical system of the endoscope, and
    joining the intermediate ring soldered to the coated cover glass into a proximal end portion of the eyecup sheath of the optical system of the endoscope.

2. The method according to claim 1, wherein solder is applied into the groove of the intermediate ring.

3. The method according to claim 1, wherein the coating can be precipitated on the intermediate ring.

4. The method according to claim 1, wherein the sheath may be a tube or part of the tube that at least partly surrounds the optical system of the endoscope or can be connected with the tube.

5. The method according to claim 1, wherein the cover glass is plexiglass.

6. The method according to claim 1, wherein the coating is applied to the cover glass by vaporization.

7. The method according to claim 1, wherein the intermediate ring is joined by cementing the intermediate ring to the sheath of the endoscope.

8. The method according to claim 1, wherein the cover glass is a curved surface.

9. The method according to claim 1, wherein the intermediate ring soldered with the coated cover glass is joined to the sheath by soldering it.

10. The method according to claim 1, wherein the coating is an anti-fog coating.

11. The method according to claim 1, wherein the coverglass protrudes beyond an inner wall of the intermediate ring.

12. The method according to claim 1, wherein the cover glass is brazed into the groove of the intermediate ring, in particular by active brazing.

13. The method according to claim 1, wherein the cover glass is soldered into the groove of the intermediate ring in that the cover glass is placed into the groove of the intermediate ring whereby a gap remains between a surrounding surface of the cover glass and an inner surface of the intermediate ring, and in that the solder penetrates into the gap upon soldering and at least partly fills it.

14. The method according to claim 1, wherein the solder forms a fillet weld between a surrounding surface of the cover glass and a ring-shaped plane surface of the intermediate ring.

15. The method according to claim 1, wherein the coating is an anti-reflecting coating.

16. The method according to claim 1, wherein the intermediate ring is joined into the proximal end portion of the eyecup sheath of the endoscope by welding.

17. The method according to claim 1, wherein the cover glass is a proximal end window of the endoscope.

* * * * *